United States Patent [19]

Miller

[11] Patent Number: 5,791,801
[45] Date of Patent: Aug. 11, 1998

[54] LIQUID APPLICATOR

[75] Inventor: Frederic D. Miller, Rockford, Ill.

[73] Assignee: Siebe North, Inc., Charleston, S.C.

[21] Appl. No.: 706,147

[22] Filed: Aug. 30, 1996

[51] Int. Cl.$^6$ .................. A61M 35/00; A47L 13/17
[52] U.S. Cl. .................................. 401/132; 604/3
[58] Field of Search ........................ 401/132; 604/3

[56] References Cited

U.S. PATENT DOCUMENTS

| | | | |
|---|---|---|---|
| 1,166,761 | 1/1916 | Higgins | 604/3 |
| 1,229,195 | 6/1917 | Hamilton | 604/3 |
| 1,309,201 | 7/1919 | Hollister | 604/3 |
| 1,375,861 | 4/1921 | Sharp | 604/3 |
| 2,333,070 | 10/1943 | Hoey et al. | 604/3 |
| 3,152,352 | 10/1964 | Kosik, Jr. | 401/132 |
| 3,393,962 | 7/1968 | Andrews | 401/132 |
| 3,891,331 | 6/1975 | Avery | 401/132 |
| 4,148,318 | 4/1979 | Meyer | 128/269 |
| 4,183,684 | 1/1980 | Avery, Jr. | 401/133 |
| 4,304,869 | 12/1981 | Dyke | 435/296 |
| 4,362,241 | 12/1982 | Williams | 206/210 |
| 4,415,288 | 11/1983 | Gordon et al. | 401/132 |
| 4,430,013 | 2/1984 | Kaufman | 401/132 |
| 4,525,091 | 6/1985 | Van Overloop | 401/134 |
| 4,563,103 | 1/1986 | Van Overloop et al. | 401/134 |
| 4,572,689 | 2/1986 | Chernack | 401/132 |
| 4,707,450 | 11/1987 | Nason | 435/295 |
| 4,784,506 | 11/1988 | Koreska et al. | 401/132 |
| 4,925,327 | 5/1990 | Wirt | 401/205 |
| 4,957,385 | 9/1990 | Weinstein | 401/132 |
| 5,098,297 | 3/1992 | Chari et al. | 433/215 |
| 5,288,159 | 2/1994 | Wirt | 401/133 |
| 5,302,358 | 4/1994 | Anderson et al. | 422/305 |
| 5,308,180 | 5/1994 | Pournoor et al. | 401/205 |
| 5,393,497 | 2/1995 | Haber et al. | 422/103 |
| 5,425,915 | 6/1995 | Phillips et al. | 422/58 |
| 5,435,660 | 7/1995 | Wirt | 401/135 |
| 5,509,744 | 4/1996 | Frazier | 401/132 |

FOREIGN PATENT DOCUMENTS

| | | | |
|---|---|---|---|
| 124290 | 3/1919 | United Kingdom | 604/3 |
| 1016053 | 1/1966 | United Kingdom | 401/132 |

*Primary Examiner*—Steven A. Bratlie
*Attorney, Agent, or Firm*—Leydig, Voit & Mayer, Ltd.

[57] ABSTRACT

A liquid applicator of the type used to apply pre-operative liquid to the body prior to surgery. The liquid is contained in a sealed ampoule. The applicator has a hollow cylindrical handle with an internal configuration which firmly seats the ampoule within the handle. A neck section of the housing, generally seated with and extending from the handle has a thin-walled section positioned very close to the neck of an ampoule supported in the handle, so that manual depression of the thin-walled section allows the operator to sever the ampoule tip from the ampoule body, allowing one-handed release of fluid prior to application.

20 Claims, 1 Drawing Sheet

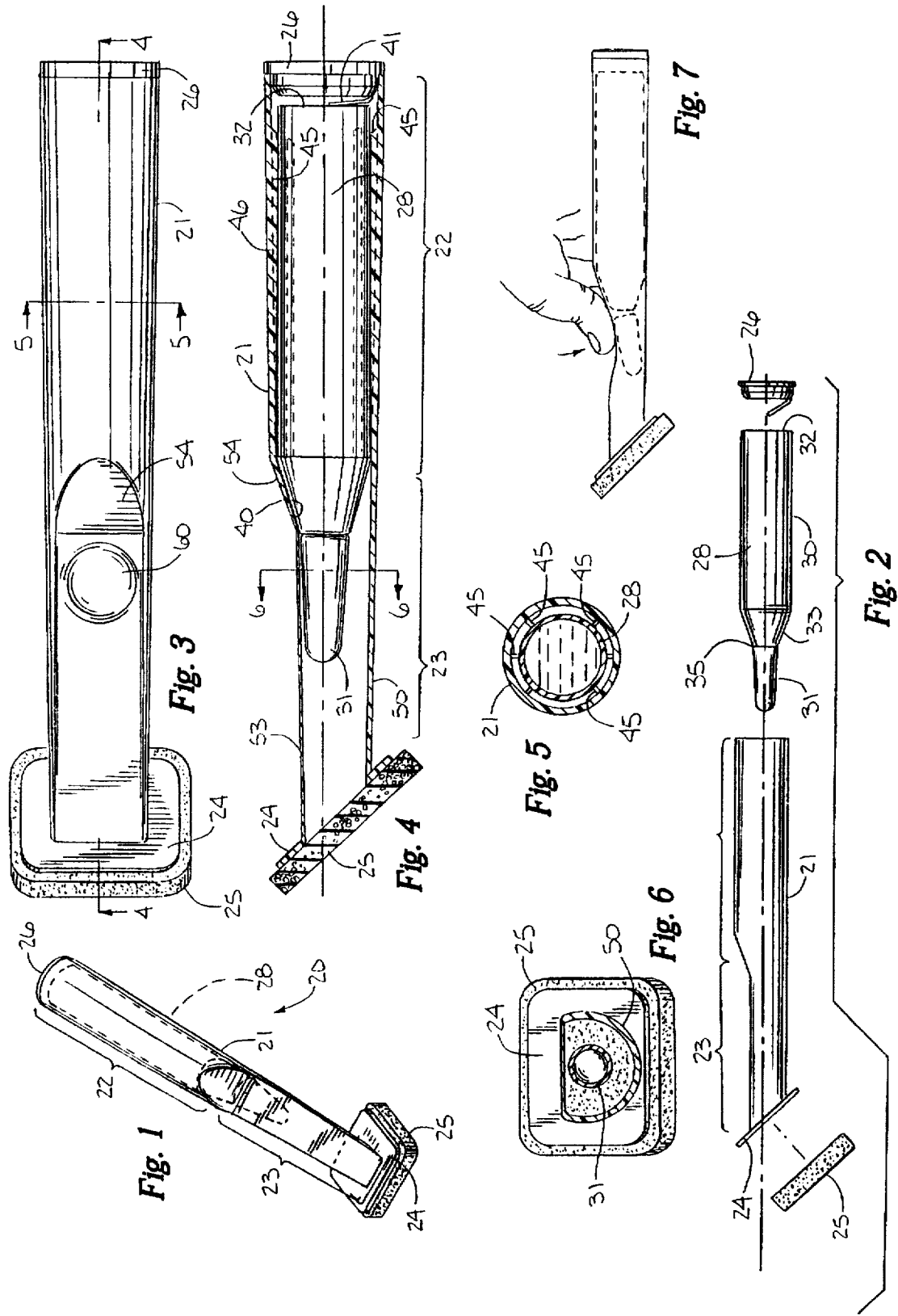

LIQUID APPLICATOR

FIELD OF THE INVENTION

This invention relates to liquid applicators, and more particularly to applicators for "scrubbing" a portion of the body with fluid prior to surgery.

BACKGROUND OF THE INVENTION

In preparing a person for surgery, it is typical to scrub the body portion of interest with an antiseptic solution. A typical prior art applicator used for this purpose is illustrated, for example, in Wirt U.S. Pat. No. 5,288,159. The antiseptic liquid, which is often an alcohol and iodine based solution, is contained within a sealed ampoule. The ampoule is carried in the handle of the applicator, and is supported in a first somewhat rearward position. Just prior to use, the base of the device is pushed forward, which drives the entire ampoule forward, ultimately causing the tip of the ampoule to engage a wedge positioned inside the applicator. That action tends to break the ampoule at a frangible score line separating the ampoule tip from the body. The fluid in the ampoule is then released to flow by gravity to a sponge affixed at the end of the applicator and disposed at an angle with respect to the handle. The device is rather rigid, so that the person applying the liquid can use a painting or scrubbing motion to vigorously apply the liquid to the body.

In this art device a vent hole is positioned near the base and a scrim is bonded to the sponge for purposes of controlling the rate of application of the liquid. These elements tend to add a measure of expense to the device.

The requirement to break the tip from the ampoule by means of sliding the ampoule forward also causes certain difficulties. First of all, care must be exercised in assembling the device to assure that the ampoule, and also the two position cap, are not pressed too far home. Secondly, separating the tip from the ampoule body requires a two handed operation. Finally, because of the constraints within the tip of the applicator, there is the possibility of wedging the severed tip in the opening of the ampoule, thus limiting the flow of solution to the sponge.

SUMMARY OF THE INVENTION

In view of the foregoing, it is an aim of the present invention to provide a fluid applicator using a sealed ampoule, in which the ampoule is securely seated within the handle of the applicator, and which provides a highly reliable means for separating the tip from the ampoule, using only one hand if desired.

A further objective of the present invention is to provide a liquid applicator of the aforementioned type which is simple in construction and assembly, and which therefore can be manufactured more economically than applicators in the prior art.

A further objective according to the present invention is provide a liquid applicator in which the ampoule is securely seated in the handle of the applicator, and need not be displaced for purposes of severing the tip.

Thus it is a corresponding feature that assembly of a liquid applicator according to the present invention can be performed simply, with the ampoule simply loaded into the handle in a well defined seated position, so that no judgment in positioning need be exercised in assembling the units.

According to one aspect of the invention, it is an object to provide an applicator which relies on deflection of a portion of the applicator housing for severing the ampoule tip, but accomplishes that without significantly impacting the overall rigidity of the applicator, so that the liquid can be applied to the body with the necessary degree of force without fear of deflecting or bending the applicator.

Finally, an objective according one aspect of the invention is to provide a relatively simple mechanism for regulating flow of the liquid from the applicator without the need for providing vents, precisely manufactured scrims, or the like.

Other objects and advantages will become apparent upon reference to the following specification when taken into conjunction with the drawings in which:

BRIEF DESCRIPTION OF THE DRAWINGS

FIG. 1 is a perspective view showing an applicator according to the present invention with the ampoule shown in position in dashed lines;

FIG. 2 is an exploded view illustrating the elements of the applicator of FIG. 1;

FIG. 3 is a plan view illustrating the applicator;

FIG. 4 is a sectional view taken along the line 4—4 of FIG. 3;

FIG. 5 is a further sectional view taken along the line 5—5 of FIG. 3 illustrating the ampoule held in position in the handle;

FIG. 6 is a sectional view taken generally along the line 6—6 of FIG. 4 and showing the tip of the ampoule and its association with the neck of the applicator; and FIG. 7 is a schematic view showing the manual depression of the thin-walled section of the neck separating the ampoule tip from the ampoule body.

While the invention will be described in connection with certain embodiments, there is no intent to limit it to those embodiments. On the contrary, the intent is to cover all alternatives, modifications and equivalents included within the spirit and scope of the invention as defined by the appended claims.

DETAILED DESCRIPTION OF THE PREFERRED EMBODIMENT

Turning now to the drawings, and particularly to FIG. 1, there is shown a liquid applicator 20 constructed in accordance with the present invention. The main structural element of the applicator 20 is a body 21 which includes an elongated handle portion 22 and a generally coaxial neck portion 23 extending therefrom. A planar applicator portion (alternatively referred to herein as a flange) 24 is disposed at an angle, such as 45° with respect to the axis of the body. A liquid dispensing foam pad 25 is affixed to the applicator portion 24. A plug 26 is adapted to close the upper end of the body. The liquid to be applied is provided by means of a sealed ampoule 28 contained within the body and supported in a conforming chamber within the handle (see FIG. 4).

Referring in greater detail to the ampoule 28, and with reference to FIGS. 2 and 4, the ampoule is a sealed glass vial containing a volume of liquid, such as approximately 25–30 milliliters of an antiseptic solution, such as the solution available commercially from 3M and sold under the trademark DURAPREP. The ampoule 28 has a cylindrical body portion 30 and a tip portion 31 opposite a closed flat end 32. Preferably a transition section, such as a sloped shoulder 33, joins the body portion 30 to the tip 31. A frangible line 35, such as a score line, is provided which serves as a weakened point for separating the tip 31 from the body 30. Pressure on the tip 31 will cause the tip to separate cleanly at the frangible line 35, releasing the fluid within the ampoule for application.

As best shown in FIG. 4, the shoulder 33 of the ampoule 28 engages a mating surface 40 on the interior of the applicator body 21, such that once the ampoule is inserted into the handle, it is adapted to seat in a fully home rest position where it is supported firmly within the handle. The plug 26 is adapted to seal the open end of the handle 22, and has a live spring hinged tab 41 which bears against the bottom 32 of the ampoule 28 to hold the ampoule firmly in its seated position.

Referring in greater detail to the applicator itself, it will be seen that it is preferably a single piece molded thermoplastic member having a hollow interior shaped to fit the ampoule. The handle portion 22 is preferably of generally cylindrical cross-section. In the most preferred embodiment, it has an inner circumference which is slightly larger than the outer circumference of the ampoule body, so that a plurality of ribs 45 (see FIG. 5) support the body of the ampoule. The walls 46 which form the handle portion 22 are relatively thick, so that the handle can be considered rigid for the purposes intended. In the illustrated embodiment, it will be seen that the cylindrical handle portion 22 is slightly tapered (approximately 1°–2°) from the base toward the neck 23. The tapering can be considered to improve the appearance, and also to assist in removal from the mold in an injection molding process which forms the handle.

In practicing the invention, the neck portion 23, which is a continuation of the handle portion 22, is of somewhat more complex shape than the handle portion. As will be seen in FIG. 6, it takes the shape of a flattened cylinder. A cylindrical portion 50 of the neck is formed as an extension of the cylindrical shape of the handle, and describes an arc which is somewhat greater than 180°. The wall thickness of the cylindrical section is about the same as the wall thickness of the handle, to provide rigidity to the neck portion 23. Thus, when the handle portion 22 is held in the hand, and the foam pad 25 is scrubbed across the body to apply the liquid, the thick-walled arcuate portion 50 provides sufficient rigidity to prevent bending or flexing of the neck portion 23.

In accordance with the invention, the neck portion is completed by a thin-walled section 53 positioned with respect to the ampoule to allow the thin-walled section to be deflected to separate the tip 31 of the ampoule from the body 30. Conveniently, the thin-walled section 53 has an intermediate tapered portion 54 (see FIGS. 3 and 4) which connects the thin-walled portion 53 with the cylindrical handle portion 22. The slope of the tapered portion 54 in the preferred embodiment is adapted to mate with the sloped shoulder 33 of the ampoule to provide a seated position of the ampoule from which it does not move. The thin-walled section 53 is flat in the preferred embodiment (see FIG. 1, for example) and as shown in FIG. 4 is positioned with respect to the axis of the ampoule to closely overlie the tip 31 of the ampoule. The flattened thin-walled section 53 can be provided with an indicia 61 (see FIG. 3) which indicates a region 60 at which manual finger pressure is to be applied in order to activate the applicator. Finger pressure in the region 60, as shown in FIG. 7, will deflect the tip 31 (while the ampoule body is held seated in the handle), causing the ampoule to break along the frangible line 35, separating the tip from the body. When the applicator is manipulated for scrubbing, with the base up and the applicator end down, the liquid will flow from the ampoule under the force of gravity down the neck portion 23 to the open end 62 of the neck.

In order to dispense the liquid thus released, the flange 24 formed at the open end of the neck 23 provides a planar surface to which is secured the foam pad 25. In contrast with prior applicators which required the use of a precisely formed hole pattern in a scrim in order to control release of liquid, in accordance with the invention, the characteristics of the foam pad 25 are matched to the flow characteristics of the liquid, so that the foam pad 25 is the primary control of rate of fluid flow from the applicator. The elimination of the scrim, which often required precisely formed laser machined holes, not only simplifies the assembly by eliminating a component, but also substantially reduces the expense related to the precisely constructed scrim.

In practicing the invention, it has been found that a compressed foam pad 25 preferably of open cell construction can serve as the primary member for regulating the rate of fluid release from the applicator. It is preferred to use a flexible polyurethane foam with a reticulated highly controlled relatively small pore size. The foam is preferably permanently compressed to a predetermined thickness. When used with the aforementioned DURAPREP solution, it is preferred to use a felted polyurethane foam available from Crest Foam Industries of Moonachie N.J., identified as #3 Compression FilterCrest Grade S-90, having a thickness of about ⅛ inches. A pad of that thickness, and approximately 2 inches square is secured to the bottom of flange 24 by means of adhesive. A suitable adhesive is a medical grade instant adhesive gel available from Loctite Corp. of Newington, Conn. and identified as Loctite #4541. The adhesive can be applied in a continuous line around the periphery of the flange 24. However, it is preferred, for purposes of economics, to use discrete glue dots in a line around the periphery.

When using the aforementioned reticulated compressed foam as the primary means of metering the rate of fluid flow from the applicator, it has been found that no separate vent is required for equalizing pressure in the applicator. The foam pad is sufficiently thick, and the flow rate of the liquid through the pad is adequate to cause wetting of the pad after breaking of the ampoule and inversion of the applicator in about 5–10 seconds, particularly when the pad is dabbed on the body. Continued scrubbing on the body and dabbing of the pad causes transfer of solution out of the pad (and air through the pad into the handle) so as to saturate the entire pad. With a pad of ⅛ inch thickness, and at a compression ratio of about 3, the pad has adequate liquid storage capacity to prevent unwanted dripping. The foam at the aforementioned compression ratio remains relatively compressible, so that scrubbing of the body or dabbing of the applicator further compresses the pad, causing release of stored liquid, and further fluid flow into the pad upon release. The user of such an applicator will soon develop a technique for controlling the release rate of fluid to the requirements of the portion of the body being scrubbed.

The material of the body is a molded thermoplastic material, preferably low density polyethylene, and even more preferably a moldable polyethylene commercially available as Rexene PE2030. The unit is preferably formed by injection molding. The wall thickness of the handle, defined herein as thick-walled, is greater than about 0.050 inches, preferably on the order of 0.060 to 0.070 inches. The dimension is not critical, but sufficient material (say at least 0.045 inches in thickness) should be used to prevent flexing of the applicator during a typical scrubbing operation. The thin-walled section, which allows deformation under manual localized pressure, is preferably less than half of the thickness of the thick-walled section, and most preferably on the order of 0.020 inches. As suggested in FIG. 6, the wall need be deformed only about 0.070 inches in one embodiment in order to reliably separate the neck from the body along the frangible line. Other shapes and configurations can be provided. However, we prefer the semi-cylindrical thick-walled section for the rigidity of the applicator and generally streamlined look, and the thin-walled flat cord disposed at the neck, preferably when marked with an indicia such as 61 or a "press here" label, as a convenient and easily used package. Other arrangements can be provided, so long as they satisfy the dual requirement of sufficient rigidity in the neck portion to minimize flexing of the applicator, yet a sufficient flexibility in the deformation section at the ampoule tip to allow localized manual pressure to deform the applicator body to separate the ampoule tip.

Referring again to FIG. 4, it will be appreciated that the shipping of the applicators constructed in accordance with the invention does not raise any significant risk of ampoule breakage. The ampoule is firmly seated in the applicator by an interengagement of the ampoule shoulder 33 with the corresponding mating surface 40 of the applicator body. The ampoule tip 31, while being positioned relatively close to the thin-walled section 53, is indeed protected from external interference, except from a very localized force applied in the region 60.

However, when it is desired to use the applicator, it is a simply a matter of gripping the applicator in the hand, and sliding the thumb forward over the region 60, whereupon slight pressure (see FIG. 7) will cause the tip to separate from the body along the frangible line 35. FIG. 4 also illustrates the fact that the hollow neck portion 23 of the applicator has a significant amount of room into which the ampoule tip can drop once separated. The applicator is typically used with the surface of the foam pad 25 horizontal, such that the base of the applicator is tilted upwardly. In that orientation, fluid flows from the ampoule by gravity. By the same token, the ampoule tip which has been separated from the ampoule can fall a distance almost equal to the length of the tip into the hollow neck, so as to avoid restricting flow from the circular opening of the ampoule. Even though the tip will be overlying a portion of the pad, the capillary flow through the pad material is adequate to ensure wetting of the entire pad and controlled release of fluid by compression and release of the pad as necessary.

It will thus be appreciated that what has been provided is a fluid applicator, such as for a surgical scrubbing, which is simple in construction and reliable in operation. The ampoule which contains the fluid is held in a fixed position in the applicator body. The applicator body is a simple injection molded unit having a handle defining an internal chamber which seats the ampoule body, a shoulder which fixes the ampoule in position and a hollow neck adapted for manual depression to release the fluid, and having adequate capacity to store the severed tip after it is broken from the ampoule. The shape of the neck portion provides the dual function of maintaining the overall rigidity of the applicator so that it can be used for scrubbing, yet provides a section which can be readily manually depressed to activate the applicator. The use of the foam pad to control release results in a product which has only four components (see FIG. 2), one of which is the fluid filled ampoule itself. The resulting economy and simplicity over the prior art structures will now be apparent.

What is claimed is:

1. A liquid applicator comprising:
   (a) a sealed, liquid-containing ampoule having a body, one end thereof including a positioning shoulder and a tip separable therefrom by a frangible section;
   (b) a housing including a generally coaxial handle and neck:
   (1) the handle defining an interior chamber adapted to enclose and protect the ampoule and shaped to engage the shoulder and support the body in a fixed position;
   (2) the neck positioned to house the ampoule tip, and having a thin-walled portion sufficiently thin to allow deflection thereof by manual pressure, and wherein the ampoule tip is disposed adjacent the thin-walled portion so that by application of sufficient manual pressure on the thin walled portion, the ampoule tip is separated from the ampoule body along the frangible section to release the liquid for application; and
   (c) a pad positioned at one end of the neck for applying the liquid.

2. The liquid applicator of claim 1, wherein the shape of the housing is generally cylindrical at the handle and of a size adequate to fixedly seat the ampoule, and in which the shape at the neck is a flattened cylinder with the flattened portion of the cylinder being the thin-walled portion.

3. The liquid applicator of claim 2, wherein the handle and the cylindrical portion of the neck have a wall thickness adequate to minimize flexing of the applicator during application of the liquid.

4. The liquid applicator of claim 3, wherein the housing is of molded polyethylene.

5. The liquid applicator of claim 3 wherein the handle and cylindrical portion of the neck have a thick-walled section that is on the order of about 0.045 inches or more in thickness, and the thin-walled portion is less than about half the thickness of the thick-walled section.

6. The liquid applicator of claim 1 in which the housing further includes a generally planar flange on the end of the neck for supporting the pad, the pad being secured to the flange.

7. The liquid applicator of claim 6 wherein the pad is adhesively secured to the flange.

8. The liquid applicator of claim 6 wherein the planar flange is oriented at an acute angle with respect to the coaxial axis of the handle.

9. The liquid applicator of claim 1, wherein the pad is a compressed foam and serves as the primary means for metering the rate of application of the liquid.

10. The liquid applicator of claim 1, further including external indicia near the thin-walled portion indicating a region thereof to be manually depressed for separating the tip from the ampoule body.

11. The liquid applicator of claim 1 further including an end cap fixedly sealing the end of the handle opposite the neck, the end cap having means engaging the ampoule for holding the ampoule in a seated position in the handle.

12. The liquid applicator of claim 11 in which the frangible section comprises a score line ringing the tip of the ampoule at its junction with the shoulder so that depression of the thin-walled portion separates the tip from the ampoule to allow free flow of liquid therefrom.

13. The liquid applicator of claim 1 in which the length of the neck is substantially greater than the length of the ampoule tip, so that after separation the tip has adequate room in the neck to drop away from the ampoule and thereby allow free flow of the liquid therefrom.

14. A liquid applicator, comprising:
   (a) a sealed, liquid-containing ampoule having a generally cylindrical body, one generally flat end and an axially extending tip of smaller diameter at the other end, a positioning shoulder between the tip and the body, and a frangible section joining the tip to the positioning shoulder;

(b) a generally cylindrical molded thermoplastic housing having a generally coaxial handle joined to a neck along an axis with a transition zone having a tapered region interposed therebetween:
  (1) the handle having a cylindrical interior chamber sized to fixedly seat the ampoule body;
  (2) the tapered region of the transition zone being adapted to engage the shoulder of the ampoule for establishing a seated position of the ampoule in the housing;
  (3) the neck being in the form of a flattened cylinder having a cylindrical portion which includes a continuation of the handle, and having a flattened portion joining the tapered portion of the transition zone, and the flattened portion being near the axis of the housing so that it is positioned adjacent the ampoule when seated in the housing, the thin-walled portion being sufficiently flexible to allow deformation thereof by sufficient manual pressure to engage the tip of the ampoule and separate the tip along the frangible section to release the liquid for application;
  (4) a planar applicator flange on the end of the neck and disposed at an acute angle with respect to the axis of the housing, the flange being open at the neck to receive the liquid for application; and
(c) a compressed foam pad secured to the flange and comprising a primary means for metering the liquid application rate.

15. The liquid applicator of claim 14 further including an end cap fixedly sealing the end of the handle opposite the neck, the end cap having means engaging the ampoule for holding the ampoule in a seated position in the handle.

16. The liquid applicator of claim 15 in which the frangible section comprises a score line ringing the tip of the ampoule at its junction with the shoulder so that depression of the thin-walled portion separates the tip from the ampoule to allow free flow of liquid therefrom.

17. The liquid applicator of claim 14 in which the length of the neck is substantially greater than the length of the ampoule tip, so that after separation the tip has adequate room in the neck to drop away from the ampoule and thereby allow free flow of the liquid therefrom.

18. A method of making a liquid applicator comprising the steps of:
  (a) providing a liquid filled ampoule having a cylindrical body, a positioning shoulder, and a tip separable therefrom by a frangible section;
  (b) molding a housing including:
    (1) a generally cylindrical handle having a chamber shaped to fixedly seat the body and engage the shoulder of the ampoule;
    (2) a neck generally coaxial with the handle and rigidly extending therefrom, and further including a thin-walled portion positioned near the handle axis and sufficiently flexible to allow application of a manual actuating force by depression of the thin-walled portion; and
    (3) a planar flange on the end of the neck opposite the housing and having an aperture into the neck;
  (c) adhesively securing a foam pad to the flange; and
  (d) securing the ampoule in the handle in a fixed position with a plug such that the ampoule tip is positioned adjacent the thin-walled portion ready for separation by a manual actuating pressure applied to the exterior thereof.

19. The method of claim 18 wherein the step of molding includes injection molding the housing as a single molded unit.

20. A method of applying liquid to a surface from a sealed ampoule fixedly held in a cylindrical chamber of a liquid applicator, and comprising the steps of:
  (a) providing a cylindrical housing having a generally rigid handle fixedly seating a body of an ampoule with an ampoule tip extending unsupported into a neck of the housing and adjacent a thin-walled portion of the neck;
  (b) providing a compressed foam pad on an applicator end of the neck;
  (c) firmly gripping the handle and momentarily depressing the thin-walled portion to separate the tip from the body of the ampoule to release the liquid for application, and
  (d) controlling the rate of application of the liquid primarily by application of a compressive force applied to the compressed foam while scrubbing the surface.

* * * * *